United States Patent
Dubois

(10) Patent No.: US 9,714,205 B2
(45) Date of Patent: Jul. 25, 2017

(54) PROCESS FOR DIRECT SYNTHESIS OF (METH)ACROLEIN FROM ETHERS AND/OR ACETALS

(71) Applicant: Arkema France, Colombes (FR)

(72) Inventor: Jean-Luc Dubois, Millery (FR)

(73) Assignee: Arkema France, Colombes (FR)

( * ) Notice: Subject to any disclaimer, the term of this patent is extended or adjusted under 35 U.S.C. 154(b) by 0 days.

(21) Appl. No.: 15/300,444

(22) PCT Filed: Mar. 26, 2015

(86) PCT No.: PCT/FR2015/050769
§ 371 (c)(1),
(2) Date: Sep. 29, 2016

(87) PCT Pub. No.: WO2015/150666
PCT Pub. Date: Oct. 8, 2015

(65) Prior Publication Data
US 2017/0113990 A1 Apr. 27, 2017

(30) Foreign Application Priority Data
Apr. 4, 2014 (FR) ...................................... 1453022

(51) Int. Cl.
| | | |
|---|---|---|
| C07C 45/38 | (2006.01) | |
| C07C 45/37 | (2006.01) | |
| B01J 23/00 | (2006.01) | |
| B01J 23/04 | (2006.01) | |
| B01J 23/881 | (2006.01) | |
| B01J 35/02 | (2006.01) | |
| B01J 35/10 | (2006.01) | |

(52) U.S. Cl.
CPC ............ *C07C 45/38* (2013.01); *B01J 23/002* (2013.01); *B01J 23/04* (2013.01); *B01J 23/881* (2013.01); *B01J 35/023* (2013.01); *B01J 35/1019* (2013.01); *B01J 35/1042* (2013.01); *B01J 35/1061* (2013.01); *C07C 45/37* (2013.01)

(58) Field of Classification Search
CPC ........ C07C 45/37; C07C 45/38; B01J 23/881; B01J 35/00
USPC ......................................................... 568/479
See application file for complete search history.

(56) References Cited

U.S. PATENT DOCUMENTS

| | | | | |
|---|---|---|---|---|
| 4,433,174 A | * | 2/1984 | Hagen | B01J 29/86 568/459 |
| 6,166,263 A | * | 12/2000 | Etzkorn | C07C 45/33 568/469.9 |
| 6,187,963 B1 | * | 2/2001 | Etzkorn | C07C 29/141 549/356 |
| 8,378,136 B2 | * | 2/2013 | Dubois | C07C 45/52 558/315 |

\* cited by examiner

*Primary Examiner* — Sikarl Witherspoon
(74) *Attorney, Agent, or Firm* — Brinks Gilson & Lione

(57) ABSTRACT

The subject matter of the present invention is a process for direct synthesis of (meth)acrolein from a reactive mixture comprising at least one compound chosen from ethers, acetals or hemiacetals derived from linear alcohols comprising from 1 to 3 carbon atoms. Examples of compounds are dimethyl ether, diethyl ether, methyl ethyl ether, dimethoxymethane, diethoxymethane, dipropoxymethane, 1,1-dimethoxyethane or 1,1-diethoxyethane. The process of the invention comprises two successive phases: oxidation then aldol condensation, which can be carried out in the presence of a solid oxidation catalyst chosen from molybdenum-based catalysts and optionally of an aldol condensation catalyst. These two phases are carried out in a reaction system comprising a single reactor or optionally two reactors in cascade.

12 Claims, No Drawings

PROCESS FOR DIRECT SYNTHESIS OF (METH)ACROLEIN FROM ETHERS AND/OR ACETALS

This application is a U.S. National Stage application of International Application No. PCT/FR2015/050769, filed Mar. 26, 2015, which claims the benefit of French Application No. 1453022, filed Apr. 4, 2014.

TECHNICAL FIELD

The present invention relates to the synthesis of unsaturated aldehydes. The subject matter is more particularly a process for direct synthesis of (meth)acrolein from a reactive mixture comprising at least one compound chosen from ethers, acetals or hemiacetals derived from linear alcohols comprising from 1 to 3 carbon atoms.

TECHNICAL BACKGROUND AND TECHNICAL PROBLEM

The term "(meth)acrolein" conventionally means acrolein or methacrolein, of formula $CH_2=CH-CHO$ or $CH_2=CH(CH_3)-CHO$, respectively.

The major known industrial processes for producing acrolein are based on various reaction schemes using different raw materials.

Processes which implement an aldol condensation reaction, as described for example in patent UK 513 772 from Degussa, use as raw materials acetaldehyde and formol which react in the gas phase by heterogeneous catalysis to form acrolein. Formol and acetaldehyde are neither stored nor transported easily; for example, formol can be transported only over a radius of 400 km around the production site, and for that must be stabilized with methanol in aqueous solution. In order to dispense with the purchasing of the raw materials, it is necessary to provide for specific units for synthesis of these products, which add to the cost of the aldol condensation unit per se. The synthesis of acetaldehyde is generally carried out by the Wacker reaction for oxidation of ethylene and the synthesis of formol is generally carried out by oxidation (or oxydehydrogenation according to the catalytic system retained) of methanol. The process for synthesis of acrolein according to the adol condensation route therefore requires considerable investments.

The industrial processes based on the oxidation of olefins, in particular the oxidation of propylene, resulting in acrolein, which has been the subject of numerous publications or patents, consume fossil raw materials extracted from oil in particular, of which the cost involved in obtaining access is becoming increasingly high. Moreover, their availability is linked to refining or petrochemical facilities with large capacities, which in practice imposes an establishment in the vicinity of large petrochemical sites, and therefore costs for transportation to the final consumer, not to mention the risks of polluting product emissions.

More recently, a new route of synthesis based on the dehydration reaction of glycerol to acrolein has been the subject of considerable works, in particular by the applicant (WO 2006/087083; WO 2006/087084; WO 2009/128555; WO 10/046227; WO 11/083225). This type of process has the advantage of being able to work with a renewable (non-fossil) natural raw material and therefore to comply with the commitments of most industrialized countries aiming to reduce greenhouse gas emissions with the environmental effects thereof, but also to provide a more sustainable production solution.

However, this route of synthesis has certain disadvantages on several levels. Indeed, the supply of glycerol depends mainly on oleochemical and/or biodiesel plants. Glycerol is only available in limited amounts which in practice restricts the possible size of the acrolein production plants and thus their economic profitability. The most widespread grades of glycerol are those known as crude glycerol, which most commonly corresponds to aqueous solutions of glycerol at 80% by weight containing salts (for example NaCl, KCl, $Na_2SO_4$, $K_2SO_4$, etc.), residual methanol when it has been obtained by methanolysis of vegetable oils, Matter Organic Non-Glycerol (MONG), and all kinds of impurities extracted from plants or animal fats during the production processes. These impurities are catalyst poisons and lead to reversible deactivation, for example by coke formation, or irreversible deactivation, for example by salt deposition. Refined glycerol is also commercially available, but at much higher prices. From a technical point of view, the dehydration catalysts known to date deactivate quickly, which necessitates regular regenerations, meaning an additional investment cost (for example doubling or tripling of the catalytic volumes). Finally, this "green" process has a drawback in that the dehydration reaction, which is carried out in the gas phase and is overall highly energy-consuming, is dependent on the cost of this energy, currently provided by fossil fuels, which also necessarily impact on the environment.

Moreover, alcohols, in particular a mixture of methanol and ethanol, have already been described as raw materials for forming acrolein. Mention may be made, for example, of application WO 2005/040392 which describes the oxidation of a mixture of methanol and ethanol in the presence of a silver catalyst, producing a mixture of acetaldehyde and formaldehyde, which is then converted to acrolein in the presence of alumina. Example 32 of said document uses a reaction mixture of which the composition is not specified, and no indication regarding the yield of the process is mentioned. This process has the drawback that the reaction temperature must be adapted to each of the steps.

With regard to the synthesis of methacrolein, industrial processes generally use, as raw materials, isobutane, tert-butanol or isobutene which are converted to methacrolein by oxidation. Other synthesis processes exist, such as oxydehydrogenation of isobutaraldehyde or hydroformylation of methylacetylene or of propadiene. Besides, in certain cases, their cost, the fossil origin of these raw materials is a major disadvantage.

Methacrolein can also be obtained by means of an aldol condensation reaction, in particular between formaldehyde and propionaldehyde according to the process described in patent U.S. Pat. No. 4,433,174, with however the drawbacks associated with the use of these aldehydes.

There therefore remains a real need to overcome the drawbacks of the (meth)acrolein synthesis processes of the prior art, in particular to reduce their impact on the environment and to limit the investments and the operating costs involved therein.

One of the objectives of the present invention is therefore to provide a process for synthesis of (meth)acrolein, using raw materials of renewable (non-fossil) origin, which is simple, rapid (comprising as few steps as possible) and easy to carry out and which gives the desired product with good selectivity.

The inventors have discovered that it is possible to synthesize acrolein and methacrolein by coupling an oxidation reaction and an aldol condensation reaction, using a reactive mixture comprising at least one compound chosen from ethers, acetals or hemiacetals derived from linear alcohols comprising from 1 to 3 carbon atoms, some of which are compounds available from renewable raw materials.

SUMMARY OF THE INVENTION

A subject of the invention is therefore a process for direct synthesis of (meth)acrolein comprising i) reacting a reactive mixture comprising at least one reactive compound, oxygen and a non-reactive diluent gas, in a reaction assembly operated in the gas phase at a temperature of between 200° C. and 400° C. and at a pressure of between 1 and 10 bar, in the presence of a solid oxidation catalyst chosen from molybdenum-based catalysts and optionally of an aldol condensation catalyst, then ii) recovering the gas effluent comprising the (meth)acrolein formed in the presence of water coproduced by the reaction, said process being characterized
in that the reaction compound(s) is (are) chosen from the compounds of formula (I) $R_1$—O—$R_2$ in which,
$R_1$ is H or a methyl, ethyl or propyl radical,
$R_2$ is a methyl, ethyl or propyl radical or a radical of formula $CH_2$—O—$R_3$, $CH(CH_3)$—O—$R_3$ or $CH(CH_2$—$CH_3)$—O—$R_3$, with $R_3$ being a methyl, ethyl or propyl radical,
with $R_1$ and $R_2$ identical or different, or $R_1$ and $R_3$ identical or different,
it being understood that, when $R_1$ is H, $R_2$ is other than a methyl, ethyl or propyl radical, failing which the reactive mixture comprises at least one other compound of formula (I) with $R_1$ other than H,
and in that the reactive compound(s) is (are) chosen such that the $R_1$, $R_2$ and $R_3$ radicals present in their structure are capable of forming (meth)acrolein by means of an oxidation reaction coupled to an aldol condensation reaction.

For the purposes of the invention, the term "process for direct synthesis" means that the synthesis is carried out in one step without isolation of intermediate compounds. This process is carried out in a single reaction assembly which comprises either a single reactor, or two successive reactors, but in this case, the second reactor is fed by the effluent leaving the first reactor.

The process of the invention is particularly advantageous since it is carried out with reactive compounds already containing an oxidized form with respect to the corresponding alcohols used as reagents. The particular choice of the reactive compound or of the combination of the reactive compounds makes it possible to limit the amount of water generated by the reaction, to limit the reverse reactions or the degradation reactions, and to thus obtain the desired product more concentrated. Furthermore, the process is carried out in a single reaction assembly, and can be performed in the presence of a single catalyst, in the presence of a molybdenum-based oxidation catalyst, thus simplifying the operating conditions for carrying out the process.

The invention is now described in greater detail and in a nonlimiting manner in the description which follows.

DETAILED DESCRIPTION OF THE INVENTION

According to the invention, use is made, as raw material for producing acrolein or methacrolein, at least one reactive compound chosen from ethers, acetals or hemiacetals derived from linear alcohols comprising from 1 to 3 carbon atoms, alone or optionally in combination with a linear alcohol comprising from 1 to 3 carbon atoms.

The reactive compound corresponds to general formula (I) $R_1$—O—$R_2$, $R_1$, $R_2$ and $R_3$ having the abovementioned meanings, and when the formula corresponds to an alcohol ($R_1$ is the hydrogen atom and $R_2$ is a methyl, ethyl or propyl radical), then at least one other compound of formula (I) which is not an alcohol is used in combination.

As examples of reactive compounds that can be used, mention may be made, without this list being limiting, of dimethyl ether (CAS 115-10-6–BP=−24.8° C.); diethyl ether (CAS 60-29-7–BP=34.6° C.); methyl ethyl ether (CAS 540-67-0–BP=7.4° C.); dimethoxymethane (CAS 109-87-5–BP=42° C.); diethoxymethane (CAS 462-95-3–BP=88° C.); dipropoxymethane (CAS 505-84-0–BP=137.6° C.); 1,1-dimethoxyethane (CAS 534-15-6–BP=64° C.); 1,1-diethoxyethane (CAS 105-57-7–BP=103° C.).

As preferred reactive compounds, mention may be made of dimethyl ether (DME), diethyl ether (DEE), dimethoxymethane (DMM), methyl ethyl ether (MEE), 1,1-dimethoxyethane (DMEt) and diethoxymethane (DEM).

These compounds are commercially available, or can be produced according to routes using renewable materials. For example, dimethyl ether (DME), just like methanol, can be produced directly from syngas. Dimethyl ether is therefore a raw material that is available in large amount and at low cost. It is also an intermediate in "methanol to propylene" processes. Moreover, it is a much better fuel than methanol.

The use of reactive compounds of ether, acetal or hemiacetal type, owing to their structure (there are 2 carbons in DME compared with 1 carbon in methanol), leads to a decrease in the molar flux and therefore in the volumetric flow, compared with the use of the corresponding alcohols. This results in advantages in particular with regard to pressure drop and compressive energy consumption in the process of the invention.

Advantageously, use is made, as reactive compounds of formula (I), of compounds which are gases at ambient temperature, such as dimethyl ether (DME), or compounds which have a low boiling point, such as, for example, diethyl ether (DEE) or dimethoxymethane (DMM). These reagents require temperatures as low as possible in order to be vaporized, or even are already gaseous, thereby making it possible to use residual streams at low levels of heat for the vaporization of the reaction feedstocks and facilitating their use in the process of the invention. The residual streams at low levels of heat are for example the streams resulting from condensation steps on the distillation columns. They are generally streams that are available on industrial sites in large amount, and at heat levels below 140° C. and preferably below 110° C., and even more preferably below 90° C. They involve for example condensed steam.

The reaction carried out in the process according to the invention is based on a first phase of oxidation of one (or more) reactive compound(s) of ether, acetal or hemiacetal type, optionally combined with an alcohol, resulting in the formation of aldehydes, which are then converted by means of an aldol condensation reaction into acrolein or (meth)acrolein.

The reactive compound(s) is (are) chosen such that the $R_1$, $R_2$ and $R_3$ radicals present in their structure are capable of forming (meth)acrolein by means of an oxidation reaction coupled to an aldol condensation reaction.

Thus, when a single reagent (I) is used, for the formation of acrolein, then $R_1$, $R_2$ or $R_3$ is a methyl or methylene radical, and at least one of the other radicals is a $CH_3$—$CH_2$ or $CH_3$—CH radical. For the formation of methacrolein, $R_1$, $R_2$ or $R_3$ is a methyl or methylene radical, and at least one of the other radicals is a $CH_3$—$CH_2$—$CH_2$ or $CH_3$—$CH_2$—CH radical.

When a mixture of reagents is used for example, for forming acrolein, a compound of formula (I) comprising at least one methyl or methylene radical ($CH_2$—) and another compound of formula (I) comprising at least one $CH_3$—$CH_2$ or $CH_3$—CH radical may be used.

To form methacrolein, a compound of formula (I) comprising at least one propyl radical and a compound of formula (I) comprising at least one methyl or methylene radical, or a mixed compound comprising a propyl or $CH_3$—$CH_2$—CH radical and a methyl or methylene radical, may be used.

As examples of reactive compounds or combinations of reactive compounds which result in acrolein, mention may be made of dimethyl ether/diethyl ether; methyl ethyl ether; dimethyl ether/diethoxymethane; diethyl ether/dimethoxymethane; dimethoxymethane/diethoxymethane; dimethoxymethane/diethoxyethane; dimethyl ether/ethanol; diethyl ether/methanol; and dimethoxymethane/ethanol.

As examples of reactive compounds or combinations of reactive compounds resulting in methacrolein, mention may be made of dipropoxymethane; dipropyl ether/methanol; and dipropyl ether/dimethyl ether.

The process according to the invention can for example be illustrated by the following reaction schemes:

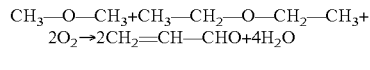

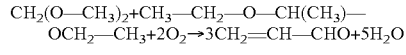

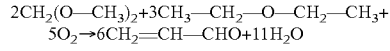

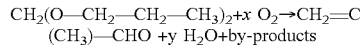

The mole ratios, calculated on the basis of the $R_1$, $R_2$ and $R_3$ radicals of the reactive compounds used, for example,
on the one hand, $(CH_3+CH_2)/(CH_3$—$CH_2+CH_3$—CH) or,
on the other hand, $(CH_3+CH_2)/(CH_3$—$CH_2$—$CH_2+CH_3$—$CH_2$—CH), are between 1 and 2 and preferably between 1.1 and 1.5.

The reaction schemes implemented in the process according to the invention require less oxygen and generate a smaller amount of water compared with the use of a mixture of alcohols according to the following reactions:

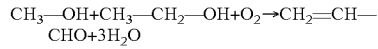

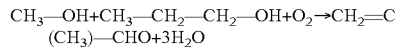

The gas effluent comprising the (meth)acrolein formed in the presence of the water coproduced by the reaction is thus more concentrated.

In addition to the reactive compound(s) of formula (I), the reactive mixture introduced into the reaction assembly comprises oxygen and a non-reactive diluent gas.

The flow rate for introducing the reactive compounds into the reaction assembly is such that their total content in the reactive mixture is between 1% and 15%, preferably between 2% and 12%, and more preferably between 2% and 6% expressed by volume.

The oxygen introduction flow rate will be such that the oxygen content of the reactive mixture will not be greater than 15%, and preferably less than 10% expressed by volume. The oxygen content of the mixture is preferably at least 1 vol %, and preferably at least 5 vol %.

Nevertheless, as long as the reactor is fitted with rupture discs or other safety devices, it is possible to operate with higher oxygen concentrations.

The remainder of the reactive mixture consists of one or more inert gases which represent about from 70% to 95% by volume of the reaction medium. The presence of the latter is essential for preventing the mixture from being located in the explosion zone. These inert gases will for example be carbon dioxide, nitrogen or a rare gas such as argon or helium. They may also be hydrocarbons, such as methanol which is inert under the reaction conditions.

The reactions in the reaction system are carried out with an HSV (hourly space velocity) generally between 2000 and 40 000 $h^{-1}$ and preferably between 5000 and 25 000 $h^{-1}$, the HSV representing the ratio between the total gas flow rate (in standard liters) divided by the volume of catalyst (apparent density taken at 1 g/ml).

In the process of the invention, use is made of a solid oxidation catalyst chosen from molybdenum-based catalysts and optionally an aldol condensation catalyst.

Oxidation catalysts have been more known for decades. In the process of the invention, a molybdenum-based, mixed-oxide solid oxidation catalyst is used.

The oxidation catalysts that can be used in the process of the invention comprise molybdenum and at least one element chosen from P, Si, W, Ti, V, Nb, Ta, Cr, Mn, Fe, Co, Ni, Cu, Zn, Ga, In, Tl, Sb, Ag, As, Ge, B, Bi, La, Ba, Sb, Te, Ce and Pb, chosen from the group consisting of mixed oxides containing molybdenum and heteropolyacids containing molybdenum.

These catalysts can be represented by the following general formula:

in which

A is at least one cation chosen from the elements of groups 1 to 16 of the Periodic Table of Elements and lanthanides, preferably a cation of an alkali metal such as Cs, Rb or K, X is P or Si, and preferably P, Z is at least one element chosen from the group comprising W, Ti, Zr, V, Nb, Ta, Cr, Mn, Fe, Co, Ni, Cu, Zn, Ga, In, Tl, Sn, Ag, As, Ge, B, Bi, La, Ba, Sb, Te, Ce and Pb and preferably Cu, Fe, Bi, Co, Ni, W, V, Cr, Sb, Mn and Ce, O is oxygen, a, b, c and d are indices consisting of whole or decimal numbers which satisfy the following ranges $0 \leq a \leq 9$ and preferably $0 < a \leq 9$ $0 \leq b \leq 2$ and preferably $0.1 \leq b \leq 1.5$ $0 < c \leq 12$ and preferably $5 < c \leq 12$ $0 \leq d \leq 12$ and preferably $0 < d \leq 4$ such that $a+b+d>0$ and e is a number determined by the total degree of oxidation of the elements.

The catalyst used during the oxidation step may be a doped or non-doped Fe—Mo—O catalyst, generally used during the oxidation of methanol to formaldehyde. Examples of iron molybdate (Fe—Mo—O) catalysts are described in *Catalysis Review*, Vol 47 (2005), pp 125-174.

These catalysts are commercially available. For example, Mapco supplies a catalyst with its technology license and Süd Chemie supplies several grades of these catalysts under the brand name FAMAX®: FAMAX J5, FAMAX MS, FAMAX HS, FAMAX TH. In the case of this type of Fe—Mo catalyst, the indices a and b of the general formula above will preferably have the value 0 and the index d will have a non-zero value.

Preferably, in particular in the variant of the process using a single catalyst, the oxidation catalyst is an iron molybdate catalyst.

The oxidation catalysts may be in bulk form and, in this case, used without support.

The catalysts may also be deposited on an inactive support, the amount of which represents from 30% to 90% and preferably at least 50% of the total weight of the catalyst.

It is possible to use, as support, any material such as steatite, silica, alumina, magnesia, titanium oxide, zirconia, silicon carbide, silicates, diatomaceous earths, borates or carbonates, or ceramics, provided that the materials are stable with respect to the operating conditions to which the catalysts are subjected.

The bulk catalyst or the supported catalyst may be in granular or powder form and may have any shape whatsoever, such as a sphere, grain, hollow cylinder, trilobe or quadrilobe, and also the shape of cylinders, which have been extruded or compressed, optionally using a pelletizing agent. Preferably, the catalyst is in the shape of hollow cylinders or hollow trilobes.

In the process of the invention, it is possible to use, in combination with the oxidation catalyst, a solid aldol condensation catalyst, for example among those known for carrying out the condensation of two aldehydes and in particular of formol with a higher aldehyde (acetaldehyde or propanaldehyde), so as to give the corresponding unsaturated aldehyde in two steps: reaction for aldol condensation of the formaldehyde to the higher aldehyde with formation of a hydroxylated aldehyde (aldol), then reaction for dehydration of this aldol.

The condensation catalysts used in the process of the invention belong to the following various categories:

1) "Supported bases", i.e. the alkali metal hydroxides LiOH, NaOH, KOH, CsOH deposited on a silica or alumina support, alkali and alkaline-earth metals dispersed on silica, alumina ($Al_2O_3$—NaOH—Na), magnesia (MgO—NaOH), charcoal or potassium carbonate, nitrogenous compounds, $NR_3$, $NH_3$, $KNH_2$ deposited on alumina, $LiCO_3$ deposited on silica, t-BuOK deposited on xonotlite and more generally solids of alkali metal type deposited on alumina (such as $Na/Al_2O_3$ or $KF/Al_2O_3$), on silica or on magnesia (such as Li/MgO).

This solid catalyst consists for example of sodium silicate deposited on silica or on aluminosilicates preferably having an Si/Al atomic ratio greater than 10 and comprising, as appropriate, a metal promoter or else cesium deposited on a silica grafted or doped with a zirconium compound (Cs—$Zr/SiO_2$);

2) "Metal oxides" BaO, BeO, SrO, CaO, $Al_2O_3$, $Y_2O_3$, $La_2O_3$, $CeO_2$, $ThO_2$, $SnO_2$, $K_2O$, $Na_2O$, MgO, ZnO, $TiO_2$, $ZrO_2$ in oxide or carbonate form optionally doped with an alkali metal, oxides or oxycarbonates of rare-earth metals optionally doped with alkali metals;

3) "Metal salts" of the above compounds, i.e. carbonates, hydroxycarbonates, hydrogencarbonates, ammonium salts, etc.;

4) "Mixed oxides" such as $SiO_2$—MgO, $SiO_2$—CaO, $SiO_2$—SrO, $SiO_2$—BaO, $SiO_2$—SnO, $SiO_2$—ZnO, $SiO_2$—$Al_2O_3$, $SiO_2$—$ThO_2$, $SiO_2$—$TiO_2$, $SiO_2$—$ZrO_2$, $SiO_2$—$MoO_3$, $SiO_2$—$WO_3$, $Al_2O_3$—MgO, $Al_2O_3$—$ThO_2$, $Al_2O_3$—$TiO_2$, $Al_2O_3$—$ZrO_2$, $Al_2O_3$—$MoO_3$, $Al_2O_3$—$WO_3$, $ZrO_2$—ZnO, $ZrO_2$—$TiO_2$, $TiO_2$—MgO or $ZrO_2$—$SnO_2$. Clay-type oxides, such as hydrotalcites, hydroxyapatites, chrysolite and sepiolite, optionally doped with alkali metals and also with metals such as copper, iron or nickel, or rare-earth metal oxides doped with alkaline earth metals, such as (SrO—$La_2O_3$), may be added to this list of mixed oxides. Other catalysts which may also be suitable for this reaction, such as mixed oxide catalysts of the mixed cobalt and aluminum phosphate type, or silica-alumina doped for example with salts of sodium (Na), potassium (K), cesium (Cs), cadmium (Cd), Mg, Ca, Sr, Mn, Zn, Mo, Nb, Pb and/or Si, are also part of this category. They may also be MgO-alumina, MgO—$SiO_2$, rare-earth metals in the form of phosphates, tungstates, molybdates, etc. Oxynitrites of phosphorus derivatives, such as mixed oxynitrites of vanadium-aluminum, phosphorus-zirconium, phosphorus-aluminum, vanadium-aluminum-phosphorus or gallium-aluminum-phosphorus may also be suitable for this reaction;

5) Various "zeolites" exchanged with alkali metal ions (Cs, K, Na, Li).

By way of example of such catalysts, mention may be made of aluminosilicates which are crystalline or amorphous, silicalites, synthetic crystalline zeolites, such as faujasite, ferrierite or ZSM-5, in their acid form or in a form either partially or totally neutralized by elements of groups 1 to 14, and preferably from groups 1 and 2 and by Zn and TI. The zeolites used may have some or all of the aluminum atoms in their structure replaced with trivalent atoms such as B, Ga, Fe, Cr, V, As, Sb, Bi or Be, and may have some or all of the silicon atoms replaced with tetravalent atoms such as Ge, Ti, Zr or Hf.

The solid condensation catalysts used in the process according to the invention have a high specific surface area, generally of between 40 and 600 $m^2/g$ and preferably between 50 and 200 $m^2/g$.

The acid-base properties of a material may be linked to its composition for example, its crystalline structure or to surface defects, such as the presence of impurities, for instance alkali metals or alkaline-earth metals.

The presence of basic sites and the amounts thereof can be determined by any known method, for example by adsorption of an acid compound such as $CO_2$ or $SO_2$, and by adsorption energy microcalorimetric measurements. The presence of acid sites and the amounts thereof can, for their part, be measured by adsorption of a basic compound such as ammonia for example.

The measurements of the acidity and basicity of the catalyst are carried out by adsorption of $SO_2$ (basicity) and of $NH_3$ (acidity) and by adsorption energy microcalorimetric measurements. The usual operating conditions are as follows.

The tests are carried out at 150° C. in a calorimeter (C80 from Setaram) connected to a conventional positive-displacement apparatus fitted with a Barocel capacitance manometer for the pressure measurements. The samples are pretreated in a quartz cell by heating overnight under vacuum at 300° C. This temperature is reached by increasing the temperature at the rate of 1° C./min. The differential heats of adsorption are measured as a function of the surface coverage by repeated passing of small doses of respective gases over the sample until an equilibrium pressure of approximately 67 Pa is reached. The sample is then degassed for 30 min at the same temperature and a second analogous adsorption series is carried out until an equilibrium pressure of approximately 27 Pa is reached. The difference between the amounts adsorbed between the first and second adsorption (at 27 Pa) represents the amount of the respective gases irreversibly adsorbed, which provides an estimate of the number of respectively acid or base strong sites.

In some cases, the acidity or the basicity of the solid is revealed only if a slight adsorption of water or alcohol is carried out beforehand on the solid. In the case of a perfectly dry atmosphere, the surface which is probably dehydrated is less acidic and/or basic. The prior adsorption of water or alcohol may be representative of the operating conditions of the reaction.

The process of the invention comprises two successive phases: oxidation then aldol condensation, which can be carried out in the presence of a single molybdenum-based oxidation catalyst. These two phases are carried out in a reaction system comprising a single reactor or optionally two reactors in cascade.

In the case in which the reaction assembly consists of a single reactor, said reactor comprises either a single fixed catalytic bed consisting of a single molybdenum-based oxidation catalyst or of a physical mixture of the two catalysts—the molybdenum-based oxidation catalyst and the condensation catalyst—, or two catalytic beds superimposed, the first (upstream) being loaded with an oxidation catalyst and the second with a condensation catalyst.

In the implementation variant with two reactors in the reaction assembly, the first reactor is used for the oxidation reaction and the second reactor is used for the aldol condensation reaction of the compounds resulting directly from the first reactor.

In this reaction assembly, the reactions are carried out in the gas phase at a temperature of between 200 and 400° C. and preferably between 250 and 350° C., at a pressure of between 1 and 10 bar absolute and preferably between 1 and 5 bar absolute.

The following examples illustrate the present invention without, however, limiting the scope thereof.

EXAMPLE 1

Synthesis of a Condensation Catalyst

The $Cs/Zr/SiO_2$ catalyst is prepared from a silica gel in the form of particles of 315 to 500 microns having a purity of 99.9%, a specific surface area of 320 $m^2/g$ and a pore volume of 0.9 $cm^3/g$ with a medium pore diameter of 9 nm.

The silica is impregnated using a solution of zirconium butoxide in butanol, filtration, and drying in a rotary evaporator and then in an oven at 120° C. for 2 hours. The impregnation and the drying were repeated 2 more times so as to obtain a deposit of 0.02% by weight (1.2 g of zirconium per 100 mol of silica). The cesium is then itself also impregnated using an aqueous solution of cesium carbonate, followed by drying, to give a cesium content of approximately 4 wt % (calculated by weight of metal). The catalyst is then calcined at 450° C. under air for 3 hours. The specific surface area of the catalyst thus prepared is 147 $m^2/g$.

EXAMPLE 2

Synthesis of a Condensation Catalyst

The $Na/SiO_2$ catalyst is prepared by impregnation of a large-pore silica gel, to which 12% by weight of sodium silicate has been added. After impregnation, the solid is dried in an oven at 100° C. for 10 h, then calcined in a furnace at 500° C. for 3 hours. The specific surface area of the catalyst prepared is 122 $m^2/g$.

EXAMPLE 3

Preparation of an Oxidation Catalyst

An iron molybdate catalyst of Mapco MS type, available in the form of pellets, which is ground so as to obtain a powder with a particle size of 40 to 80 microns, is used. This powder is then placed in the feed hopper of a coating machine, and beads of steatite of the brand name CeramTec, with an average diameter of 4.5 mm, are placed in the coating machine. The coating machine (of granulating pan type) is then rotated and an aqueous solution of glycerol at 25 wt % is sprayed onto the steatite beads, while at the same time adding the previously ground iron molybdate powder such that it adheres to the steatite beads. The beads are then dried at 150° C. The iron molybdate content in the supported catalyst thus formed is 20 wt %.

EXAMPLE 4

The coating of steatite beads is reproduced as described in example 3 with the catalysts of examples 1 and 2 after grinding in the form of a powder with a particle size of between 40 and 80 microns.

EXAMPLE 5

Synthesis of Acrolein in the Presence of a Mixture of Catalysts 100 ml of a mixture of oxidation catalyst prepared in example 3, of supported iron molybdate type, and of supported condensation catalyst of $Na/SiO_2$ type (referred to as Na in table 1) or $Cs/Zr/SiO_2$ (referred to as Zr in table 1), prepared according to example 4, is introduced into a reactor having a 2 cm internal diameter.

The flow rate of injection of the gas feedstock preheated to 120° C. is 33 l/minute, i.e. 2000 l/h. The reaction mixture (ether/acetal/alcohol) is injected while liquid into an evaporator in which it encounters the other gases, with the exception of the dimethyl ether which is injected in the gas state.

The gas mixture of the feedstock comprises from 6 to 10 vol % of oxygen, and a mixture of ether, acetal and/or alcohol in the vol % proportions indicted in table 1, the remainder to 100% being nitrogen.

The liquid mixture is fed by a pump, and goes through an evaporator before rejoining the gas stream upstream of the reactor.

The reactor is placed in an electric oven. The reaction is carried out at a pressure very slightly above atmospheric pressure and at a temperature ranging from 300° C. to 330° C.

The effluents are analyzed by chromatography with an FID detector (flame ionization detector) and with a chromatograph equipped with a methanizer-FID detector couple.

The results obtained are given in table 1 below.

The product yields are calculated by taking into account the number of carbons in the reagents and products.

Thus, the acrolein yield is: 3×(number of moles of acrolein detected)/(number of moles of C1 entering+2×number of moles of C2 entering).

C1 denotes the compounds of the reaction feedstock comprising radicals containing a single carbon atom, and C2 denotes the compounds of the reaction feedstock comprising radicals containing two carbon atoms.

TABLE 1

| Test | Catalyst ml | T, °C | MeOH | EtOH | DME | DEE | DMM | DEM | $O_2$ | Acrolein yield % mol |
|---|---|---|---|---|---|---|---|---|---|---|
| 1 | FeMo 75/Na 25 | 325 | — | — | 2.5 | 2.5 | — | — | 7 | 45 |
| 2 (comp) | FeMo 50/Na 50 | 330 | 5 | 5 | — | — | — | — | 10 | 32 |
| 3 | FeMo 50/Zr 50 | 320 | — | 5 | | | 1.5 | — | 9 | 42 |
| 4 | FeMo 25/Zr 75 | 300 | | | 1 | | | 2.5 | 6 | 35 |

DME dimethyl ether;
DEE diethyl ether;
DMM dimethoxymethane;
DEM diethoxymethane

EXAMPLE 6

Synthesis of Acrolein in the Presence of an Oxidation Catalyst

Only the catalyst of iron molybdate type obtained in example 3 is loaded to the reactor used in example 5. The HSV of the reaction feedstock is 15 000 $hr^{-1}$.

The reactor is fed with a DMM/DEE mixture in a mole ratio of 1.2, with a total partial pressure of reactants of 6%, and an oxygen partial pressure of 6%, for a total pressure of 1 atmosphere (absolute).

The major products detected are acrolein and 'acetaldehyde. The acrolein yield at 325° C. is 25%. The acrolein was produced in the presence of solely the supported iron molybdate catalyst.

EXAMPLE 7

The process is carried out as in the previous example, but using as oxidation catalyst the catalyst ACF-4 from Nippon Shokubai, which is a bismuth molybdate catalyst used in particular for the oxidation of propylene to acrolein. The grade chosen is that corresponding to a size of approximately 5 mm. As for the previous preparations, the catalyst is ground and coated on steatite beads.

The reaction is carried out at 300° C., with 100 ml of catalyst. The feedstock comprises dipropoxymethane at a content of 2 vol %, and oxygen at a content of 4%. The HSV is 7000 $hr^{-1}$.

Methacrolein was obtained with a yield of 12%.

The invention claimed is:

1. A process for direct synthesis of (meth)acrolein comprising i) reacting a reactive mixture comprising at least one reactive compound, oxygen and a non-reactive diluent gas, in a reaction assembly operated in the gas phase at a temperature of between 200° C. and 400° C. and at a pressure of between 1 and 10 bar, in the presence of a solid oxidation catalyst chosen from molybdenum-based catalysts and optionally of an aldol condensation catalyst, and then ii) recovering gas effluent comprising the (meth)acrolein formed in the presence of water coproduced by the reaction, wherein the at least one reactive compound comprises a compound of formula (I) $R_1$—O—$R_2$ wherein,
$R_1$ is H or a methyl, ethyl or propyl radical, and
$R_2$ is a methyl, ethyl or propyl radical or a radical of formula $CH_2$—O—$R_3$, $CH(CH_3)$—O—$R_3$ or $CH(CH_2$—$CH_3)$—O—$R_3$, with $R_3$ being a methyl, ethyl or propyl radical,
wherein $R_1$ and $R_2$ are identical or different, or $R_1$ and $R_3$ are identical or different, and
wherein, when $R_1$ is H, $R_2$ is other than a methyl, ethyl or propyl radical, failing which the reactive mixture comprises an additional reactive compound of formula (I), having $R_1$ other than H, and
wherein the at least one reactive compound is chosen such that the $R_1$, $R_2$ and $R_3$ radicals present in its structure are capable of forming (meth)acrolein by an oxidation reaction coupled to an aldol condensation reaction.

2. The process as claimed in claim 1, wherein the reactive mixture is reacted in the presence of a solid oxidation catalyst chosen from molybdenum-based catalysts and the presence of an aldol condensation catalyst.

3. The process as claimed in claim 1, wherein the at least one reactive compound comprises dimethyl ether, diethyl ether, methyl ethyl ether, dimethoxymethane, diethoxymethane, dipropoxymethane, 1,1-dimethoxyethane or 1,1-diethoxyethane.

4. The process as claimed in claim 1, wherein when acrolein is synthesized, the at least one reactive compound comprises dimethyl ether/diethyl ether; methyl ethyl ether; dimethyl ether/diethoxymethane; diethyl ether/dimethoxymethane; dimethoxymethane/diethoxymethane; dimethoxymethane/diethoxyethane; dimethyl ether/ethanol; diethyl ether/methanol; or dimethoxymethane/ethanol.

5. The process as claimed in claim 1, wherein when methacrolein is synthesized, the at least one reactive compound comprises dipropoxymethane; dipropyl ether/methanol; or dipropyl ether/dimethyl ether.

6. The process as claimed in claim 1, wherein the flow rate for introduction of the at least one reactive compound into the reaction assembly is such that a total content of the at least one reactive compound in the reactive mixture is between 1% and 15% by volume.

7. The process as claimed in claim 1, wherein the oxygen introduction flow rate is such that an oxygen content of the reactive mixture is not greater than 15% by volume.

8. The process as claimed in claim 1, wherein the reaction is carried out with an hourly space velocity of between 2000 and 40,000 $h^{-1}$.

9. The process as claimed in claim 1, wherein the oxidation catalyst is represented by the following general formula:

$$A_aX_bMo_cZ_dO_e \quad (I)$$

in which
A is at least one cation selected from the group consisting of the elements of groups 1 to 16 of the Periodic Table of Elements and lanthanides, X is P or Si, Z is at least one element selected from the group consisting of W, Ti, Zr, V, Nb, Ta, Cr, Mn, Fe, Co, Ni, Cu, Zn, Ga, In, Tl, Sn, Ag, As, Ge, B, Bi, La, Ba, Sb, Te, Ce and Pb, O is oxygen, a, b, c and d are indices comprising whole or decimal numbers which satisfy the following ranges $0 \leq a \leq 9$ $0 \leq b \leq 2$ $0 < c \leq 12$ $0 \leq d \leq 12$ such that $a+b+d>0$ and e is a number determined by the total degree of oxidation of the elements.

10. The process as claimed in claim 1, wherein the reaction is carried out in a single reactor with a catalytic bed comprising a single molybdenum-based oxidation catalyst or optionally a physical mixture of a molybdenum-based oxidation catalyst with a condensation catalyst.

11. The process as claimed in claim 10, wherein the reaction is carried out in a single reactor with a catalytic bed comprising a physical mixture of a molybdenum-based oxidation catalyst with a condensation catalyst.

12. The process as claimed in claim 1, wherein the reaction is carried out in a single reactor with two superimposed catalytic beds, the oxidation catalytic bed being placed upstream of the condensation catalytic bed.

* * * * *